(12) United States Patent
Jolivet-Reynaud et al.

(10) Patent No.: US 7,785,586 B2
(45) Date of Patent: Aug. 31, 2010

(54) MONOCLONAL ANTIBODIES DIRECTED AGAINST HEPATITIS B VIRUSES

(75) Inventors: Colette Jolivet-Reynaud, Saint Bonnet de Mure (FR); Mylene Lesenechal, Villeurbanne (FR); Nicole Battail-Poirot, Lyons (FR); Laurence Becquart, Saint Priest (FR)

(73) Assignee: Biomerieux SA, Marcy-l'Etoile (FR)

( * ) Notice: Subject to any disclaimer, the term of this patent is extended or adjusted under 35 U.S.C. 154(b) by 897 days.

(21) Appl. No.: 10/399,668

(22) PCT Filed: Oct. 12, 2001

(86) PCT No.: PCT/FR01/03169

§ 371 (c)(1),
(2), (4) Date: Sep. 8, 2003

(87) PCT Pub. No.: WO02/34789

PCT Pub. Date: May 2, 2002

(65) Prior Publication Data

US 2004/0219154 A1 Nov. 4, 2004

(30) Foreign Application Priority Data

Oct. 20, 2000 (FR) .................................. 00 13454

(51) Int. Cl.
*A61K 39/395* (2006.01)
*A61K 39/00* (2006.01)
*C12N 7/00* (2006.01)

(52) U.S. Cl. ............... 424/130.1; 434/184.1; 435/235.1
(58) Field of Classification Search .................... None
See application file for complete search history.

(56) References Cited

U.S. PATENT DOCUMENTS

| | | | |
|---|---|---|---|
| 5,204,095 A * | 4/1993 | Goodall et al. ........... | 424/149.1 |
| 6,030,616 A | 2/2000 | Waters et al. | |
| 6,099,840 A * | 8/2000 | Thomas et al. ........... | 424/139.1 |
| 6,541,011 B2 * | 4/2003 | Punnonen et al. ......... | 424/204.1 |

FOREIGN PATENT DOCUMENTS

| | | | |
|---|---|---|---|
| WO | WO 95/16704 | 6/1995 | |
| WO | WO 97/40164 | * 10/1997 | ............... 424/218.1 |

OTHER PUBLICATIONS

Tavares et al. Active and passive immunization in the extremely preterm infant. 2005, Journal de Pediatria, vol. 81, p. 89-94.*
Ishioka et al. Journal of Immunology, 1999, vol. 162, p. 3915-3925.*
Norder et al. Journal of General Virology, 1993, vol. 74, p. 1341-1348.*
W.P. Paulij et al., "Localization of a unique hepatitis B virus epitope sheds new light on the structure of hepatitis B virus surface antigen", Journal of General Virology, vol. 80, No. 8, Aug. 1999, pp. 2121-2126, XP002174119.
M. P. Cooreman et al., "Characterization of the reactivity pattern of murine monoclonal antibodies against wild-type hepatitis B surface antigen to G145R and other naturally occuring "a" loop escape mutations", Hepatology, vol. 30, No. 6, Nov. 1999, pp. 1287-1292, XP001015475.
C. Joloviet-Reynaud et al., "Localization of hepatitis B surface antigen epitopes present on variants and specifically recognised by anti-hepatitis B surface antigen monoclonal antibodies", Journal of Medical Virology, (Oct. 2001) 65 (2) 241-9, XP002195005.
S. Ijaz et al., "Novel immunoassay for the detection of hepatitis B surface 'Escape' mutants and its application in liver transplant recipients", Journal of Medical Virology, vol. 63, No. 3, Mar. 2001, pp. 210-216, XP001015468.

* cited by examiner

*Primary Examiner*—Zachariah Lucas
*Assistant Examiner*—Agnieszka Boesen
(74) *Attorney, Agent, or Firm*—Young & Thompson

(57) ABSTRACT

The present invention relates to a monoclonal antibody capable of binding to a wild-type HBsAg antigen and to at least one, preferably at least two and advantageously more than two, mutant forms of the HBsAg antigen, said monoclonal antibody binding to a peptide sequence consisting of at least 6 contiguous amino acids in the 199-208 region of the HBsAg antigen, and advantageously binding to the peptide sequence constituted by the 199-208 region of the HBsAg antigen.

16 Claims, 1 Drawing Sheet

```
                    10                  20                  30
M E N I T S G F L G P L L V L Q A G F F L L T R I L T I P Q 40                  50                  60
S L D S W W T S L N P L G G T T V C L G Q N S Q S P T S N H 70                  80                  90
S P T S C P P T C P G Y R W M C L R R F I I F L F I L L L C 100                 110                 120
L I F L L V L L D Y Q G M L P V C P L I P G S S T T S T G P 130                 140                 150
C R T C M T T A Q G T S M Y P S C C C T K P S D G N C T C I 160                 170                 180
P I P S S W A F G K F L W E W A S A R F S W L S L L V P F V 190                 200                 210
Q W F V G L S P T V W L S V I W M M W Y W G P S L Y S I L S
                      H P L K Q Y W W R P S I                     SEQ ID NO: 14
                              H W W K H P T R Y S L G             SEQ ID NO: 12
                    220
P F L P L L P I F F C L W V Y I                                   SEQ ID NO: 5
```

FIGURE 1

SEQUENCE LISTING

<160> NUMBER OF SEQ ID NOS: 14

<210> SEQ ID NO 1
<211> LENGTH: 10
<212> TYPE: PRT
<213> ORGANISM: Hepatitis B virus

<400> SEQUENCE: 1

Trp Tyr Trp Gly Pro Ser Leu Tyr Ser Ile
 1               5                  10

<210> SEQ ID NO 2

```
<211> LENGTH: 12
<212> TYPE: PRT
<213> ORGANISM: Hepatitis B virus

<400> SEQUENCE: 2

His Pro Leu Lys Gln Tyr Trp Trp Arg Pro Ser Ile
 1               5                  10

<210> SEQ ID NO 3
<211> LENGTH: 12
<212> TYPE: PRT
<213> ORGANISM: Hepatitis B virus

<400> SEQUENCE: 3

His Trp Trp Lys His Pro Thr Arg Tyr Ser Leu Gly
 1               5                  10

<210> SEQ ID NO 4
<211> LENGTH: 30
<212> TYPE: DNA
<213> ORGANISM: Hepatitis B virus

<400> SEQUENCE: 4
tggtattggg ggccaagtct gtacagcatc                                      30

<210> SEQ ID NO 5
<211> LENGTH: 226
<212> TYPE: PRT
<213> ORGANISM: Hepatitis B virus

<400> SEQUENCE: 5

Met Glu Asn Ile Thr Ser Gly Phe Leu Gly Pro Leu Leu Val Leu Gln
 1               5                  10                  15

Ala Gly Phe Phe Leu Leu Thr Arg Ile Leu Thr Ile Pro Gln Ser Leu
                20                  25                  30

Asp Ser Trp Trp Thr Ser Leu Asn Pro Leu Gly Gly Thr Thr Val Cys
            35                  40                  45

Leu Gly Gln Asn Ser Gln Ser Pro Thr Ser Asn His Ser Pro Thr Ser
        50                  55                  60

Cys Pro Pro Thr Cys Pro Gly Tyr Arg Trp Met Cys Leu Arg Arg Phe
 65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Met Thr Thr Ala
            115                 120                 125

Gln Gly Thr Ser Met Tyr Pro Ser Cys Cys Cys Thr Lys Pro Ser Asp
        130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220
```

Tyr Ile
225

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctcatagt tagcgtaacg                                              20

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Lys Met His Ser His Pro Arg Leu Thr Ser Pro
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Trp Gly Asn His Ser Lys Ser His Pro Gln Arg
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp His Lys Ala Val Pro Arg Trp Leu Ala Ser Pro
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Met Ala His Arg Trp Gln Ser Phe Leu Arg Pro
 1               5                  10

<210> SEQ ID NO 11
<211> LENGTH: 12
<212> TYPE: PRT
<213> ORGANISM: Artificial Sequence
<220> FEATURE:

```
-continued

<223> OTHER INFORMATION: Description of Artificial Sequence: Synthetic
      peptide

<400> SEQUENCE: 11

Arg Val His Lys Arg His Arg Thr Gln Lys Asn Ala
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Trp Trp Lys His Pro Thr Arg Tyr Ser Leu Gly
  1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Phe Phe Lys Leu Ser Asn Trp Arg Thr Thr Pro
  1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Pro Leu Lys Gln Tyr Trp Trp Arg Pro Ser Ile
  1               5                  10
```

MONOCLONAL ANTIBODIES DIRECTED AGAINST HEPATITIS B VIRUSES

Five types of viral hepatitis, hepatitis A, B, C, D, E, are fairly well known at present. In each case, the virus invades the liver and causes an inflammatory state with destruction of the hepatic cells.

Hepatitis B is caused by a virus, the human hepatitis B virus (HBV). The HBV virus was discovered by Blumberg et al. A "new" antigen in leukemia sera, JAMA 191: 541, (1965). The virus is transmitted via the blood route, by sexual contact or via the perinatal route.

HBV infection in the majority of cases produces no symptoms and is responsible for asymptomatic acute hepatitis. Acute hepatitis is characterized by digestive disorders, abdominal pains, abnormal coloration of the urine and discoloration of the faeces, asthenia and jaundice. Acute hepatitis can develop into a fulminant form with rapid necrosis of the liver.

The viral infection can also develop into a chronic form, either in patients having had acute hepatitis, or in individuals for whom the infection was asymptomatic. Chronic carriers have hepatic lesions of variable size and an increased risk of developing cirrhosis and primitive cancer of the liver. In Asia and in Africa where chronicity of the infections is frequent, primitive cancers of the liver represent a crucial public health problem. Moreover, chronic carriers represent reservoirs for the virus and allow its propagation, transposing the public health problem to global level.

HBV infection is one of the most common viral infections in humans. This is a ubiquitous disease with a distinct geographical incidence. In Europe and North America between approximately 0.1% and 1% of the population is infected, whilst in Asia and Africa up to 20% of the population are carriers of HBV. The number of persons infected by HBV world-wide is estimated at approximately 350 million.

Listing viral infections following a transfusion in order shows that transmission of HBV is first, followed by HCV and then HIV.

HBV is a small virus with DNA 42 nm in diameter which belongs to the group of hepatotropic DNA viruses (hepadnaviruses) and is classified in the *Hepadnaviridae* family. Its genomic structure is remarkably compact. The virus comprises an outer envelope and a nucleocapsid. The envelope is chiefly composed of three surface antigens (HBsAgs: hepatitis B surface antigens) which play a major role in the diagnosis of HBV infections. The nucleocapsid contains the core antigen (HBcAg), a DNA polymerase/reverse transcriptase, as well as the viral genome. The viral nucleus constitutes the infectious element of the virus and the outer membrane carries the principal antigenic determinant of the virus, the HBs antigen. The viral nucleus remains inside the nucleocapsid. Its diameter is approximately 28 nm.

In spite of its small size (3200 base pairs) the circular, partially double-stranded DNA of HBV codes for four types of viral products from its overlapping S, C, P, and X genes.

The S gene codes for the HBsAg envelope protein expressed on the outer surface of the virion. The HBsAg envelope protein is constituted by two major polypeptides, a 24-kDa polypeptide and its 28-kDa glycosylated form. HBsAg contains the major neutralizing epitope of HBV, called the "a" determinant, which corresponds to the amino acids 124 to 147 and is common to all the isolates of HBV. The "a" determinant is the most important target for diagnosis and vaccination. The development of anti-HBs antibodies after an acute or chronic infection is generally associated with recovery and a favourable prognosis. The anti-HBs antibodies are also associated with the production of neutralizing antibodies after vaccination. The majority of the anti-HBs antibodies found in the serum of convalescent individuals or after vaccination bind to the "a" determinant region. Although the three-dimensional structure of the HBs antigen has not yet been defined, structure-function studies indicate that the "a" determinant is localized in the main hydrophilic region of the HBsAg antigen (residues 99 to 169). It is clear that the "a" determinant is highly structured because denaturation of this zone by alkylation or reduction produces HBsAg particles; the antigenicity of which is drastically reduced. It is probable that disulphide bridges between cysteines are involved in a correct conformation. A potential structure of the "a" determinant (residues 124-147), which comprises five cysteines, would imply the existence of disulphide bridges between the amino acids 124 and 137, forming a first loop, and between the amino acids 139 and 147, forming a second loop. The whole of the "a" determinant sequence probably contributes to the antigenic structure. Moreover, the HBsAg antigen contains either the d or y determinant which corresponds respectively to the presence of either a lysine or an arginine at position 122 and, either the w or r determinant which corresponds respectively to the presence of either a lysine or an arginine at position 160. There are therefore four major antigenic sub-types of HBsAg, adw, ayw, adr and ayr, each being associated with a geographical distribution. Upstream of the S gene, the Pre-S genes code for various HBV surface antigens.

The P gene codes for the DNA polymerase/reverse transcriptase, which is very important in the viral replication mechanism.

The C gene codes for two nucleocapsid proteins, HBeAg which is a soluble secreted protein and HBcAg, the intracellular core protein. HBeAg is a serological marker of increased viral replication.

The X gene codes for HBxAg which has different biological effects and which can in particular transactivate the transcription of viral and cellular genes.

When HBV infects an individual, the viral DNA is replicated totally inside the host's hepatic cells.

Following HBV infection, the first marker detectable in the patient's serum is the HBsAg antigen, but this marker rarely persists beyond six months. After the HBs antigen has disappeared from the serum, the anti-HBsAg antibodies become detectable and persist. Because the HBc antigen is sequestered by the HBs envelope antigen, it is not routinely detectable in the serums of patients, but the presence of anti-HBc antibodies is easily identified within one to two weeks following the appearance of the HBs antigen.

However it is now certain that the standard serological tests, using the above-mentioned markers, do not make it possible to detect the variants of HBV. The fact that patients who are carriers of HBV and who have developed chronic hepatitis B exist, without it being possible to identify an HBV infection using the standard serological markers, is of the utmost importance and shows the need to develop better tests.

The existence of HBV variants has been suspected for a number of years. This assumption is based on the detection of viral DNA in the serum and/or liver of patients with chronic hepatitis, in the absence of identification of the standard serological markers (HBsAg and anti-HBc).

The inability to detect HBsAg in patients who are carriers of DNA sequences of the virus could have several explanations, such as a low expression of the surface antigen or the presence of mutations at the level of the antigenic determinant of the S protein. In the first case, a viral co-infection could suppress the replication of HBV (Jilg W et al., J. Hepatol, 1995, 23: 14-20, Jylberberg et al., Clinical infection diseases, 1996, 23: 1117-1125, Ushida et al., J. of Med. Virol. 1997, 52: 399-405, Hofer et al., Eur. J. Clin; Microbiol. Infect. Dis., 1998, 17: 6-13. Another explanation could be that the HBs antigen is masked during the in vivo formation of immune complexes with the anti-HBs antibodies.

But, more recently, the presence of HBsAg has been observed in patients' anti-HBs serums. The presence of the HBsAg antigen in these patients could be linked to the fact that it has not been neutralized by the anti-HBs present, suggesting the presence of variants.

The presence of variants or mutants has been associated with vaccination and therapy using polyclonal or monoclonal antibodies. The analysis of mutants seems to show that they have been selected from a mixed population and have point mutations causing amino acid substitutions in the "a" determinant. The mutants seem to be the product of random mutations in the gene which lead to a pool of genotypes. Moreover it is thought that the immune response is the predominant factor in the selection of the mutants. Generally, the addition of monoclonal antibodies to cells infected by a virus in vitro leads to a selection of isolates which are not neutralized by the antibodies. It is therefore not surprising that monoclonal antibodies given to patients with an active viral replication can result in a selection of escape mutants. Several separate escape mutants of clinical importance have been found in vaccinated individuals. In several cases, they have a point mutation at the level of the codon which codes for amino acid 145 in the "a" determinant of the HBsAg antigen, resulting in the change of a glycine to arginine. The administration of serum containing such a mutant to a chimpanzee has shown that these agents are transmissible. Another point mutation inducing the replacement of a lysine by a glutamic acid at position 141 of the "a" determinant has also been found in vaccinated patients. It is therefore important to be able to detect, in a sure and reliable manner, not only wild-type HBV, but also the mutants or variants. In fact, if a significant mutation occurs at the level of the HBsAg epitope and it is not recognized by the anti-HBs antibodies then, either the mutant will not been detected, or the test will not be sufficiently sensitive. Now, the fact that an escape mutant has not been detected not only affects the person carrying it, but can also lead to transmission of the infection by donations of blood, blood products and organs. Moreover, a mutant HBsAg can infect individuals even if they have been previously immunized and have an anti-HBs-type response. In International Patent Application WO 94/26904, a monoclonal antibody has been described which makes it possible to distinguish the wild-type form of HBsAg from an escape mutant which comprises a mutation at position 122. But, there is a serious need to characterize monoclonal antibodies which are capable of detecting both the wild-type and mutant forms of the HBsAg antigen for the development of reliable diagnostic tests (Coleman et al. (1999), Journal of Medical Virology 59: 19-24; Ireland et al. (2000), Hepatology 31: 1176-1181). In fact, in certain cases, mutant forms of HBV affecting the region of the envelope gene coding for the "a" determinant are not recognized by the monoclonal antibodies used in commercial diagnostic tests (Carman et al. (1990), Lancet 336: 325-329; Seddigh-Tonekaboni et al. (2000), Journal of Medical Virology 60: 113-121; Weinberger et al. (2000), Journal of General Virology 81: 1165-1174).

Thus a subject of the present invention is a monoclonal antibody capable of binding to a wild-type HBsAg antigen and to at least one, preferably at least two and advantageously more than two, mutant forms of the HBsAg antigen, said monoclonal antibody binding to a peptide sequence consisting of at least 6 contiguous amino acids in the 199-208 region of the HBsAg antigen, and advantageously binding to the peptide sequence constituted by the 199-208 region of the HBsAg antigen.

Also, a subject of the present invention is a monoclonal antibody which is capable of binding specifically to a wild-type HBsAg antigen, and to at least one, preferably at least two and advantageously more than two, mutant forms of the HBsAg antigen, said monoclonal antibody binding specifically to the 199-208 region of the HBsAg antigen.

The capacity of the monoclonal antibody of the present invention to bind specifically to wild-type and mutant forms of the HBsAg antigen is connected to the fact that it recognizes a highly preserved region of the surface antigen, as shown for the first time by the inventors by the "mapping" of epitopes, in both the wild-type and mutant forms of HBV which correspond to the region or epitope located between the amino acids 199 and 208 of the HBsAg antigen, irrespective of the presence of other mutations or amino acid substitutions which can occur at the level of the "a" determinant or in the vicinity of the "a" determinant of the HBsAg antigen. Thus, the monoclonal antibody of the invention is capable of recognizing and of binding specifically to at least one mutant form of the HBsAg antigen which comprises at least one amino acid substitution in the "a" determinant of the HBsAg antigen and, in particular, mutant forms of the HBsAg antigen which have at least one amino acid substitution at positions 127, 133, 134, 142, 143, 144 and 145 of the "a" determinant of the HBsAg antigen and optionally at least one other amino acid substitution at positions 100, 118, 120, 122 of the HBsAg antigen. The mutations or substitutions identified are located with reference to the amino acid sequence of the wild-type HBsAg antigen.

The mutant forms which are specifically recognized by the monoclonal antibodies of the invention are identified in the following examples. These are more specifically the following mutants:

1043 Sp in which a serine at position 143 of the HBsAg antigen is replaced by a leucine, AP 3.1 in which an aspartic acid at position 144 of the HBsAg antigen is replaced by an alanine, Arg 1.2 in which a glycine at position 145 of the HBsAg antigen is replaced by an arginine, 1157 Sp in which a proline at position 127 of the HBsAg antigen is replaced by an alanine and a serine at position 143 of the HBsAg antigen is replaced by a leucine, 1056 Sp in which a proline at position 120 of the HBsAg antigen is replaced by a serine and a serine at position 143 of the HBsAg antigen is replaced by a leucine, and M5 in which a tyrosine at position 100 of the HBsAg antigen is replaced by a serine, a threonine at position 118 of the HBsAg antigen is replaced by a valine, an arginine at position 122 of the HBsAg antigen is replaced by a lysine, a methionine at position 133 of the HBsAg antigen is replaced by an isoleucine, a tyrosine at position 134 of the HBsAg antigen is replaced by an asparagine, a proline at position 142 of the HBsAg antigen is replaced by a serine, a serine at position 143 of the HBsAg antigen is replaced by a leucine, and a glycine at position 145 of the HBsAg antigen is replaced by a lysine.

The abovementioned mutants can be used for the screening of monoclonal antibodies. The antibodies of the invention can, for example, be screened against the wild-type HBsAg antigen and against one or more mutants as described above. In particular, the antibodies of the invention can be screened against the wild-type HBsAg antigen and against one or more HBsAg mutants each having one or more substitutions at least one of the positions 127, 133, 134, 142, 143, 144 and 145 of the HBsAg antigen, more particularly at least one of the positions 143, 144 and 145 of the HBsAg antigen and optionally at least one other substitution at least one of the positions 100, 118, 120, 122 of the HBsAg antigen.

In particular, the monoclonal antibodies of the invention are capable of binding to a wild-type HBsAg antigen and to at least one mutant HBsAg carrying an "a" determinant coded by sequences having point mutations at the level of one or more codons coding for the amino acids 127, 133, 134, 142, 143, 144 and 145 of the HBsAg antigen. The preferred antibodies of the invention are the antibodies referenced 2G2G10 and 8B4H7 which belong to the immunoglobulin G class. The 2G2G10 monoclonal antibody belongs to the IgG2b immunoglobulin class. The 8B4H7 monoclonal antibody belongs to the IgG2a class and has been obtained by UV treatment of the 2G2G10 antibody.

The present invention also includes the fragments and derivatives of the monoclonal antibodies of the invention, in particular the Fab, Fab', F(ab)2 and sFv fragments (Blazar et al., 1997, Journal of Immunology 159: 5821-5833 and Bird et al., 1988, Science 242: 423-426), as well as the conjugates. The monoclonal antibody derivatives of the invention include, inter alia, the humanized antibodies. The methods for producing fragments of monoclonal antibodies and derivatives of monoclonal antibodies, including the humanized derivatives, are well known to a person skilled in the art. The "humanized" forms of non-human, for example murine, antibodies, are chimeric antibodies which include a minimal sequence derived from a non-human immunoglobulin. Most of the humanized antibodies are human immunoglobulins (receptor antibodies) in which residues of a hypervariable region of the receptor are replaced by residues of a hypervariable region of a non-human donor species (donor antibodies), such as mouse, rat, rabbit or non-human primate, having the desired specificity, affinity and capacity. In certain cases, the (FR) residues of the Fv region of the human immunoglobulin are replaced by corresponding non-human residues. Moreover, the humanized antibodies can contain residues which are not found in the recipient antibody or in the donor antibody. These modifications are carried out in order to improve the performances of the antibody. In general, the humanized antibody will include at least one and preferably two variable domains, in which all or almost all of the hypervariable loops correspond to a non-human immunoglobulin and all or almost all of the FR regions are those of a human immunoglobulin. The humanized antibodies can optionally also include at least one part of a constant region (Fc) of an immunoglobulin, such as a human immunoglobulin (Jones et al., Nature 321: 522-525 (1986); Reichmann et al., Nature 332: 323-329 (1988); and Presta et al., Curr. Op. Struct. Biol. 2: 593-596 (1992).

The monoclonal antibodies of the invention and, in particular the 2G2G10 and 8B4H7 antibodies, are produced by hybridoma lines according to the protocol described in Example 1 which follows, or according to a protocol derived from that described in Example 1 and a subject of the invention is also such a process for production of the monoclonal antibodies of the invention which consists of producing a hybridoma line by immunizing a mammalian animal, preferably a murine animal, with a wild-type HBsAg antigen or a mutant form of an HBsAg antigen, optionally in the form of a fragment or an appropriate antigen derivative, by immortalizing the antibody-producing cells in order to form hybridomas, by screening the hybridoma cultures against the wild-type HBsAg antigen and at least one mutant form as defined previously, optionally in the form of a fragment or an appropriate antigen derivative, and by selecting the hybridomas which produce antibodies which bind to the wild-type HBsAg antigen and to at least one mutant form as defined above.

The invention also includes a hybridoma capable of producing a monoclonal antibody of the invention and a process for producing a monoclonal antibody of the invention, which consists of cultivating a hybridoma or liable to be obtained according to a process as defined above, in vitro or in vivo, and recovering the monoclonal antibody from the culture medium; as well as a monoclonal antibody liable to be obtained by the hybridoma culture process.

The monoclonal antibodies of the invention can be used in an immunoassay for the detection and/or quantification of the HBsAg antigen in a sample assumed to contain it, and therefore for the detection of (wild-type and/or mutant) HBV viruses. Such assays can be used in clinical diagnosis and in the screening of blood products. Also, the present invention relates to a process for the detection and/or quantification of HBsAg antigen in a sample, which consists of bringing the sample into contact with at least one monoclonal antibody of the invention, or a fragment or derivative of such a monoclonal antibody and identifying the presence of at least one antigen/antibody, fragment or derivative complex.

In one embodiment of the process of the invention, the sample is brought into contact with a monoclonal antibody of the invention, or a fragment or derivative thereof and with at least one other antibody chosen from the polyclonal or monoclonal anti-HBsAg antibodies directed against a region or epitope different from that recognized by the monoclonal antibodies, fragments or derivatives of the invention.

Such processes are carried out according to the "sandwich" or "competition" technique well known to a person skilled in the art, in one or two stages, in homogeneous or heterogeneous phase. Moreover, the processes of the invention can be linked, in the same assay, to the detection of anti-HBc antibodies in the sample to be analysed.

The corresponding diagnostic compositions include at least one monoclonal antibody of the invention, or a fragment or derivative thereof, optionally in combination with at least one reagent for the detection of anti-HBc antibodies and can moreover include at least one other monoclonal or polyclonal antibody for the detection of the HBsAg antigen which recognizes a region or epitope different from that recognized by the monoclonal antibodies, fragments or derivatives of the invention. The antibodies, fragments or derivatives of the invention can be immobilized on a solid phase, as HBsAg antigen capture antibodies or used in detection when marked with any appropriate marker. It is also envisaged to use the antibodies, fragments or derivatives of the invention as an HBsAg antigen capture phase and to use at least one other monoclonal or polyclonal antibody directed against an epitope different from that recognized by the antibodies of the invention as a detection conjugate, or vice versa. Similarly, the antibodies, fragments or derivatives of the invention and at least one other monoclonal or polyclonal antibody directed against an epitope different from that recognized by the antibodies of the invention can be immobilized on the same solid phase. And moreover, a reagent capable of capturing the anti-HBc antibodies in the sample can be immobilized on this same solid phase or included in a composition of the invention but by being immobilized on a solid phase different from that on which the antibodies, fragments or derivatives of the invention are immobilized and optionally at least one other anti-HBsAg monoclonal or polyclonal antibody recognizing an epitope different from that recognized by the antibodies of the invention.

The invention also relates to a antiserum appropriate for a therapeutic or prophylactic use for a passive immunization against HBV which comprises a monoclonal antibody of the invention or a fragment or derivative of such an antibody or their combinations. The antiserum can moreover include at least one monoclonal antibody or polygonal antibody or a mixture of anti-HbsAg monoclonal and polyclonal antibodies, other that the monoclonal antibody, fragment or derivative of the invention.

An appropriate composition for a therapeutic or prophylactic use for a passive immunization against HBV comprises a monoclonal antibody, or a fragment or derivative of the invention or their combinations, in a mixture with a pharmaceutically acceptable vehicle.

By "pharmaceutically acceptable vehicle" is meant the supports and vehicles which can be administered to humans or animals, as described for example in Remington's Pharmaceutical Sciences 16$^{th}$ ed., Mack Publishing Co.

The invention therefore moreover comprises a method of passive immunization with a therapeutic or prophylactic aim against HBV which consists of administering to an individual a therapeutically or prophylactically effective quantity of a monoclonal antibody, fragment or derivative of the invention or their combinations. One or more other anti-HBsAg monoclonal or polyclonal antibodies directed against an epitope different from that recognized by the antibodies, fragments or derivatives of the invention can also be administered.

The invention also includes an anti-idiotype or anti-idiotypic antibody to an antibody of the invention as defined above. The anti-idiotype antibody is an antibody which is produced against another antibody and which reacts with the specific antigen-binding site of the latter or idiotype. The anti-idiotype antibodies function as the antigen recognized by the idiotype. Such antibodies are particularly useful in the case of conformational epitopes. The anti-idiotype antibodies which represent the internal image of external pathogens, such as viruses, are used as "substitutes" for the antigens for the vaccination. The importance of the anti-idiotype antibodies in vivo has been demonstrated in a number of experiments. The administration of anti-idiotype antibodies in vivo has the effect of either suppressing or enhancing responses to the specific idiotype. The anti-idiotype antibodies of the invention are capable of inducing a response in the animal by production of anti-anti-idiotype antibodies which recognize the 199-208 epitope of the HBsAg antigen and are therefore capable of immunizing an animal against HBV, even of neutralizing an HBV infection. Thus, a subject of the present invention is a vaccinal composition which comprises a quantity sufficient to immunize an animal against HBV, of an active composition comprising an anti-idiotype monoclonal antibody which induces in the animal the production of an anti-anti-idiotype antibody which recognizes the 199-208 region of the HBsAg antigen or a Fab fragment of said anti-idiotype antibody or their mixture and a pharmaceutically acceptable adjuvant, for example aluminium hydroxide or aluminium phosphate. The pharmaceutically acceptable adjuvants are well known to a person skilled in the art and the adjuvants mentioned in Remington's Pharmaceutical Sciences 16$^{th}$ ed., Mack Publishing Co. can be given as a reference. If desired, the vaccine can contain minor quantities of auxiliary substances such as wetting or emulsifying agents, agents which buffer the pH. The process for immunizing an animal against HBV consists of administering to it, in one or more administrations, a vaccinal composition as defined above. Of course, after the in vivo tests on animals, the ultimate aim of a vaccination against the HBV virus is to prevent an infection in humans. Thus, the term "animal" as used above refers to both animals and humans. The vaccine is prepared by mixing the anti-idiotype antibody of the invention or its Fab fragment in an appropriate diluent, which can be an aqueous phosphate buffer inter alia, so as to obtain a final concentration of the order of 1 mg per ml of protein. For administration to a human of normal size, for example, 50 µl (50 µg) to 100 µl (100 µg) of the solution are diluted in 4 500 µl and mixed with 500 µl of a pharmaceutically acceptable adjuvant (pH 6.0+0.1). The dose will vary depending on the animal, its age and its weight.

The idiotype monoclonal antibodies of the invention are produced by techniques well known to a person skilled in the art. The 199-208 epitope or region of the HBsAg antigen is obtained and purified by any technique currently available. The idiotype antibody (Ab1) is produced by immunizing an animal, preferably murine, and in particular a mouse, with the abovementioned epitope, as antigen. The animal's spleen cells are then identified, isolated and fused with lymphoma or myeloma cells in the presence of a fusion agent such as polyethylene glycol (Köhler and Milstein, Nature 256:459 (1975)). The fused cells are then incubated in a selective medium which inhibits the growth of the non-fused malignant cells. The hybridoma cells are cloned by limiting dilution and tested for the secretion of a monoclonal antibody of sought specificity. The monoclonal antibodies can also be obtained by growth of ascites in vivo. The idiotype antibody Ab1 is used in order to produce an anti-idiotype antibody (Ab2) which has the properties of immunization, even of neutralization, against HBV. The anti-idiotype antibodies Ab2 are obtained by the same processes as those used for the production of the antibodies Ab1, but the antibody Ab1 is then the immunogen used.

A subject of the invention is also the conserved epitope of the HBsAg antigen identified by the inventors, the peptide sequence of which, represented in the identifier of sequences SEQ ID NO: 1, starts at amino acid 199 and ends at amino acid 208 of the HBsAg antigen and its use as immunogenic peptide, as well as immunogenic peptides characterized in that their peptide sequence comprises respectively at least three and at least four amino acids homologous or identical to the amino acids of the epitope referenced in SEQ ID NO: 1, in particular the immunogenic peptides illustrated in SEQ ID NO: 2 and SEQ ID NO: 3. In the comparison of the sequences SEQ ID NO:1 and SEQ ID NO: 2 illustrated in the annexed figure, the sequence SEQ ID NO: 2 includes three amino acids, W (tryptophane), P (proline), S (serine) which are strictly homologous or identical to the corresponding amino acids of SEQ ID NO:1 and one amino acid I (isoleucine) which is equivalent to L (leucine) of SEQ ID NO:1. In the comparison of the sequences SEQ ID NO:1 and SEQ ID NO: 3 illustrated in the annexed figure, the sequence SEQ ID NO: 3 includes four amino acids which are strictly homologous or identical to those of SEQ ID NO: 1, these are the amino acids W (tryptophane), P (proline), Y (tyrosine), S (serine), and two amino acids T (threonine) and L (leucine) which are equivalent respectively to S (serine) and I (isoleucine) of SEQ ID NO:1. The said equivalent amino acids are amino acids which can be substituted for one other without affecting the immunogenic power of the peptides. Such immunogenic peptides are used for the production of monoclonal antibodies, fragments of monoclonal antibodies or derivatives of monoclonal antibodies corresponding to the definitions given previously and capable of recognizing both the wild-type form and at least one mutant form of the HBsAg antigen. The production of monoclonal antibodies, of fragments or derivatives of monoclonal antibodies is well known to a person skilled in the art. Köhler and Milstein, Nature 256: 45-47 (1975) and European Journal of Immunology 6: 511-519 (1976) as well as Galfre G. et al. Nature, 266: 522-550 (1977) can be mentioned as examples. The epitope can be produced by chemical synthesis or by genetic recombination or by a combination of different methods. The sequence coding for the epitope of the invention can thus be expressed in an appropriate host cell under the control of an appropriate promoter. The host cells include any unicellular organism capable of transcribing and translating recombinant DNA molecules, such as the cells derived from a prokaryotic or eukaryotic organism including the cells of mammals, yeasts and bacteria, and allowing the expression of the fragment of the S gene coding for the epitope of the invention, the fragment of the gene being placed under the control of the elements necessary to its expression. Moreover, the immunogenic peptides SEQ ID NO: 2 and SEQ ID NO: 3 can easily be obtained by chemical synthesis.

The invention finally relates to a nucleic probe or primer capable of hybridizing, under specific stringent conditions, to a DNA nucleotide sequence which codes for the epitope represented in SEQ ID NO: 1 or to the complementary DNA nucleotide sequence of said nucleotide sequence coding for the epitope represented in SEQ ID NO: 1 or to the RNA transcription product of said DNA nucleotide sequences.

The invention also relates to a nucleic probe or primer capable of hybridizing, under specific stringent conditions, to a DNA nucleotide sequence represented in SEQ ID NO: 4 which codes for the epitope represented in SEQ ID NO: 1 or to the complementary DNA nucleotide sequence of SEQ ID NO: 4 or to the RNA transcription product of said nucleotide DNA sequences; a diagnostic composition comprising at least one probe or at least one primer as defined above for the detection and/or quantification of (wild-type and/or mutant) HBV viruses in a biological sample and a process of diagnosis of DNA and/or RNA of (wild-type and/or mutant) HBV viruses in a biological sample, according to which a biological sample, such as serum, plasma or tissue sample is taken from a patient suspected of being infected by at least one HBV virus, if necessary said sample is treated in order to extract the DNA and/or the RNA from it, said sample is brought into contact with at least one probe or at least one primer, under specific stringent conditions, and the viral DNA and/or RNA in the sample is detected and/or quantified, either by identifying a hybridization of said viral DNA and/or RNA with at least one probe, or by amplification of said DNA and/or RNA. In the case of the use of nucleotide probes, the identification of the formation of the hybridization complex can be carried out directly by use of a complementary or approximately complementary probe of the target sequence and marked by any appropriate marker or also by implementation of the "sandwich" technique in one or two stages which consists of using a complementary or approximately complementary capture probe of one part of the target sequence and a probe marked by any appropriate marker or complementary or approximately complementary detection probe of another part of the target sequence. In the case of use of primers, these can be directly marked for the identification of a marked amplification product or not be marked, in which case the amplification products generated can be selected as a function of the expected size, by passing over acrylamide gel or analysed using appropriate detection probes. Starting from the selection of the DNA nucleotide sequence which codes for the 199-208 epitope of the invention, corresponding to the nucleotides 751-780 of the HBV genome described by Galibert et al. (Nature 280: 646-650 (1979), represented in SEQ ID NO: 4, of its complementary sequence and of the corresponding RNA sequence, it is within the capability of a person skilled in the art to determine and obtain nucleotide probes or primers capable of being hybridized to SEQ ID NO: 4, to its complementary sequence or to the corresponding RNA sequence. As examples for the production of oligonucleotides, the use of restriction enzymes and chemical synthesis using an automatic synthesizer can be mentioned. The probes and primers capable of hybridizing under specific stringent conditions to a DNA or RNA nucleotide sequence of the invention form part of this definition. It is within the capability of a person skilled in the art to define the appropriate stringent conditions. Characteristic stringent conditions are those which correspond to a combination of the temperature and saline concentration chosen between approximately 12 and 20° C. below the Tm ("melting temperature") of the hybrid studied. All this forms part of the general knowledge of a person skilled in the art and the teaching given in the book entitled "DNA PROBES" by George H. Keller and Mark M. Manak, Second Edition, edited in 1993 by Stockton Press, 49 West 24$^{th}$ St., New York, N.Y. 10010, USA (see more particularly: Section 1-Molecular Hybridization Technology, pp. 1-21) can be mentioned by way of illustration.

FIG. 1

The annexed FIG. 1 represents the amino acid sequence of the HBsAg antigen (SEQ ID NO: 5). In this figure the 199-208 epitope is located, identified by "mapping" of epitopes as illustrated in the following examples. The two clones HWWKHPTRYSLG (SEQ ID NO: 3) and HPLKQYW-WRPSI (SEQ ID NO: 2) which have common or homologous or identical amino acids and amino acids equivalent to the amino acids of the sequence of the wild-type HBsAg antigen in the region comprised between the amino acids 194-209 of the amino acid sequence of the HBsAg antigen are represented below the sequence of the wild-type HBsAg antigen. The common or homologues or identical and equivalent amino acids are represented in bold type in FIG. 1.

EXAMPLES

Example 1

Production and Characterization of the Monoclonal Antibodies

Female BALB/c JYco mice, aged 4 to 6 weeks (IFFA Credo), were immunized by intraperitoneal injection of 50 μg of recombinant HBsAg ay emulsified with an equal volume of Freund's complete adjuvant. The recombinant HBsAg ay protein was obtained from Pasteur Merieux Connaught. This protein corresponds to the ayw strain sequenced by Gallibert et al. (Nature 280: 646-650 (1979)) and has been expressed in CHO cells (Michel et al., PNAS 81/7708-7712 (1984)). It is composed of the pre-S and S regions. The 55 amino acids situated at the NH$_2$ terminal position correspond to the pre-S2 region.

Three injections were then carried out every two weeks in the presence of incomplete adjuvant. Four days after the last injection, the spleen cells were removed and fused with the myeloma cell line of Sp 2/0-Ag14 mice, according to the technique described by Köhler & Milstein (Nature 256: 45-47 (1975); European Journal of Immunology 6: 511-519 (1976)). After culturing the cells for 12 to 14 days, the culture supernatants were screened by an indirect ELISA test with the recombinant ay plasmatic HBsAg antigen fixed on the solid phase. One thousand and fifty eight culture supernatants, diluted $1/10^{th}$, were thus screened. Sixty six positive clones were selected for which the OD at 405 nm was approximately 2, i.e. six times higher than the threshold value, at this same wavelength, of 0.3. The sixty six culture supernatants of the positive clones, diluted $1/10^{th}$, were then screened by an indirect ELISA test with native ay plasmatic HBsAg antigen. Twenty clones were selected for which the OD at 405 nm was greater than 2, i.e. 24 times higher than the threshold value, at this same wavelength, of 0.1. The culture supernatants of 12 of these 20 clones, diluted $1/10^{th}$, were then tested by an indirect ELISA test, respectively with native ay HBsAg antigen and native ad HBsAg antigen, fixed on the solid phase. Six clones were selected from each of these tests, for which the OD at 405 nm was 1.2 or more for the test with the native ay HBsAg antigen and approximately 1.1 for the test with the native ad HBsAg antigen, at a $1/1600^{th}$ dilution of the culture supernatant, i.e. an OD approximately ten times higher than the threshold value of 0.1. Four of these six positive clones were sub-cloned twice by limiting dilution and produced in the form of ascites. The ascites were obtained from mice having received an injection of Pristane (commercial name) beforehand, and into which $10^6$ hybridoma cells were injected.

The four IgGs thus obtained were purified over a column of sepharose coupled to the A 4FF protein, according to the protocol supplied by the manufacturer (Pharmacia) and were used for the following experiments. Finally, the 2G2G10 monoclonal antibody, which belongs to the IgG2b class of immunoglobulins was retained due to its excellent performances.

Example 2

Change of Class of the 2G2G10 Antibodies

The class of the 2G2G10 monoclonal antibodies was changed from IgG2b to IgG2a by UV treatment according to the protocol of Rosen and Klein (Nature 306: 189-190 (1983)). The modified antibody was named 8B4H7.

Example 3

Screening of a Bank of Peptides Carried by Phages

The Ph.D.-12™ bank marketed by New England Biolabs Inc. was screened by the biotinylated 2G2G10 and 8B4H7 monoclonal antibodies according to the method described by Gretch et al. (Analytical Biochemistry 163: 270-277 (1987)). This is a combinatorial bank of dodecapeptides expressed at the N-terminal position of a minor envelope protein (pIII) of the M13 phage. It contains approximately $4.10^{12}$ phages/ml, representing $1.9.10^9$ different sequences.

During the first "biopanning", 10 µg of streptavidin in 0.1 M NaHCO$_3$ buffer (pH 8.6) is fixed in a Petri dish 35 mm in diameter, overnight, at 4° C., in a humid chamber, under stirring. The dish is then saturated for 2 hours at 4° C. with a saturation solution [5 mg/ml BSA; 0.02% NaN$_3$ in 0.1M NaHCO$_3$ (pH 8.6)]. After 6 washings in TBS (Tris Buffer Saline) [0.5 M Tris; 0.75 M NaCl, pH 7.5]-0.1% Tween, the biotinylated 2G2G10 or 8B4H7 monoclonal antibodies are incubated at a concentration of 170 nM in TBS 0.1% Tween with 0.02% NaN$_3$ and 1 mg/ml of BSA overnight at 4° C., in a humid chamber and under stirring. In order to block the sites not occupied by the antibody, 40 µg of biotin are added and incubated for 1 hour at 4° C., in a humid chamber and under stirring. After 6 washings in TBS 0.1% Tween, 10 µl of the bank ($4.10^9$ phages) diluted in TBS 0.1% Tween-0.1 nM biotin are incubated for 1 hour at ambient temperature, under stirring. The non-fixed phages are then eliminated by 10 washings in TBS 0.1% Tween. Elution of the fixed phages is carried out by incubation for 7 minutes with the elution buffer [0.1M HCl-Glycine; pH 2.2; 1 mg/ml BSA; 0.1 mg/ml of phenol red]. The eluate is neutralized by 200 µl of 1M Tris-HCl pH 9.1.

The eluates corresponding to the screenings of the bank, either with 2G2G10, or with 8B4H7 are amplified separately by infection of the ER2537 strain of *Escherichia coli* in LB medium [tryptone 10 g/l; yeast extract 5 g/l; NaCl 10 g/l; pH 7.5]. After incubation for 4 hours and 30 minutes at 37° C. at 250 rpm, the cellular debris was eliminated by two successive 10-minute centrifugations at 10 000 rpm. The phages contained in the supernatants are precipitated twice with $1/6^{th}$ of polyethylene glycol/NaCl [16.7% polyethylene glycol, 3.3 M NaCl]. After centrifugation for 15 minutes at 14 000 rpm, the pellets are taken up in 200 µl of TBS-0.02% NaN$_3$. 100 µl of these amplified eluates are used for the second biopannings.

For the $2^{nd}$, $3^{rd}$ and $4^{th}$ "biopannings", 100 µl of the preceding amplified eluates are preincubated with respectively 100 nM, 1 nM and 0.1 nM of the biotinylated 2G2G10 or 8B4H7 antibodies overnight at 4° C., while 10 µg of streptavidin is fixed on a Petri dish, as previously. The phage/antibody mixtures are added after saturation of the dishes for 15 minutes at ambient temperature. The protocol is continued in a manner similar to that of the first "biopannings".

Example 4

Cloning and Amplification of Phage Clones

A culture of *E. coli* is incubated at 37° C. at 250 rpm until the optical density (OD) reaches 0.5. During the bacterial growth, top agarose [1 1 LB; 10 g bacto-tryptone; 5 g yeast extract; 5 g NaCl; 1 g MgCl$_2$, 6H$_2$O; 7 g agarose] is melted and aliquoted by 3 ml, and stored at 55° C. When the cells are ready, 200 µl of culture is incubated for 1 to 5 minutes at ambient temperature with 10 µl of the eluate obtained after the $4^{th}$ biopannings and diluted in LB medium. The mixtures are then transferred into 2 tubes of agarose, vortexed and rapidly plated on LB IPTG/XGal dishes. The dishes are incubated overnight at 37° C.

36 colonies chosen at random from the dishes corresponding to screening by 2G2G10 or 8B4H7 are amplified by infection with 1 ml of a culture of *E. coli* for 4 to 5 h at 37° C., then the cells are eliminated by centrifugation for 30 seconds at 14 000 rpm. 500 µl of the supernatant is used for the sequencing, the remainder is centrifuged again, diluted 1:1 in glycerol and stored at −20° C.

2 µl of phages stored in LB/Glycerol are amplified by infection with 1.7 ml of a culture of *E. coli* for 24 hours at 37° C. and 250 rpm. The cells are eliminated by centrifugation for 5 minutes at 14 000 rpm. The supernatant is precipitated by PEG/NaCl. After centrifugation for 15 minutes at 14 000 rpm, the pellet is taken up in 500 µl of TBS. These phage solutions are assayed by absorption spectrometry at 269 nm and used for the ELISA tests.

Example 5

Sequencing of the Sequences Inserted into the Phage Clones

The extraction and purification of the DNA of the different clones are carried out starting from 500 µl of supernatant which is precipitated by 200 µl of PEG/NaCl for 10 minutes at ambient temperature. After centrifugation for 10 minutes at 14 000 rpm, the pellet is taken up in 100 µl of 10 mM Tris-HCl pH 8.0, 1 mM EDTA, 4M NaI and 250 µl of absolute ethanol then incubated for 10 minutes at ambient temperature. After centrifugation for 10 minutes at 14 000 rpm, the pellet is washed once using 500 µl of 70% ethanol, then dried for 10 minutes under vacuum. It is finally taken up in 30 µl of 10 mM Tris-HCl pH 8.0, 1 mM EDTA.

The nucleotide sequencing of the insert is carried out according to Sanger's modified method using an automatic sequencer (model 377A, Perkin Elmer) using the "Big Dye™ Terminator Cycle Sequencing Ready Reaction" (Perkin-Elmer) sequencing kit and the 5'HO-CCCTCATAGT-TAGCGTAACG-OH3' (SEQ ID NO: 6) primer corresponding to the wild-type sequence of the phage. The reaction mixture comprises 5 µl of DNA to be sequenced, 2.5 pmoles of oligonucleotides in 2.5 µl of water, 8 µl of "Big Dye™" mixture containing the didesoxyribonucleotides and the Taq™ polymerase, and 4.5 µl of $H_2O$. The 25 sequencing cycles (30 seconds at 96° C., 15 seconds at 50° C., 4 minutes at 60° C.) are carried out in Trioblock PCR (Polymerase Chain Reaction) device from Biometra. The sequence fractions are purified on a Sephadex G50 column equilibrated with TE [10 mM tris-Hcl pH8, 1 mM EDTA] buffer, dried and stored at −20° C. until sequencing. The protein sequences are deduced from the nucleotide sequences using the Geneworks software,

Example 6

Immunological Analysis of the Phage Clones

100 µl of the 2G2G10 or 8B4H7 anti-HBsAg antibodies or of a non-pertinent antibody used as a negative control at the final concentration of 100 µg/ml in 0.1 M $NaHCO_3$ buffer are fixed overnight at 4° C., in a humid chamber, on rows of ELISA "Nunc Maxisorb" well plates. The plate is then saturated for 2 hours at 4° C. in saturation solution [0.1 M $NaHCO_3$; BSA 50 mg/ml; $NaN_3$ 0.02%]. After 4 washings in TBS-0.5% Tween, 100 µl of different concentrations of phages diluted in TBS Tween ($1.10^{12}$, $2.5.10^{11}$, $6.2.10^{10}$ and $4.10^9$ phages/ml) are added per well and incubated for 2 hours at ambient temperature, under stirring. After 4 washings in TBS 0.5% Tween, 100 µl/well of anti-M13 antibodies coupled with peroxidase and diluted 1/5000 in saturation solution is incubated for 2 hours at ambient temperature, under stirring. After incubation for 1 hour at 37° C., the plate is washed 4 times in TBS-0.5% Tween. For development, the plate is incubated with a solution of o-phenylenediamine and hydrogen peroxide (colorEIA kit, bioMerieux) for 10 minutes in obscurity. The reaction is stopped by 1.8 N sulphuric acid and the plate is read at 492 nm, with an ELISA plate reader (Axia microreader). For each dilution of each clone the results are expressed by the difference in the values obtained between the anti-HBsAg antibody and the control antibody. The results are then confirmed by testing the optimal dilutions in triplicate.

No immunoreactive clone could be selected by the 2G2G10 antibody. On the other hand, the equivalent 8B4H7 antibody having the same paratope but of class IgG 2a allowed selection of the immunoreactive clones (Table 1). Moreover two of these clones (HWWKHPTRYSLG (SEQ ID NO: 3) and HPLKQYWWRPSI (SEQ ID NO: 2)) are also recognized by the 2G2G10 antibody.

TABLE 1

Frequency and immunoreactivity of the phage clones selected with the 2G2G10 antibody and the modified 8B4H7 antibody.

| Clone sequence | Clone frequency | Reactivity with 8B4H7[a] | | Reactivity with 2G2G10[b] |
|---|---|---|---|---|
| HKMHSHPRLTSP (SEQ ID NO: 7) | 13/36 | <0.1[c] | | |
| HWGNHSKSHPQR (SEQ ID NO: 8) | 6/36 | <0.1 | | |
| WHKAVPRWLASP (SEQ ID NO: 9) | 4/36 | 0.8 | 0.4[d] | <0.1[e] |
| HMAHRWQSFLRP (SEQ ID NO: 10) | 2/36 | <0.1 | | |
| RVHKRHRTQKNA (SEQ ID NO: 11) | 1/36 | >2.5 | <0.1 | |
| HWWKHPTRYSLG (SEQ ID NO: 12) | 1/36 | >2.5 | 0.5 | >2.5 |
| HFFKLSNWRTTP (SEQ ID NO: 13) | 1/36 | 22.5 | <0.1 | |
| HPLKQYWWRPSI (SEQ ID NO: 14) | 1/36 | <0.1 | | 0.4 |

The immunoreactivity of the clones was determined by ELISA as indicated in Example 6, with 8B4H7[a] or 2G2G10[b] fixed on the solid phase and the phage clones added to the final dilution of $8 \times 10^{10}$ phages/ml[c] and $2 \times 10^{10}$ phages/ml[d].

Example 7

Location of the Immunoreactive Phage Clone Sequences on the HbsAg Sequence

The amino acid sequences of the peptides were compared to the HBsAg recombinant protein sequence used to obtain the monoclonal antibody (Galibert et al., 1979) using the Mac Vector software, Ver.4.5 (Kodak). Briefly, the regions of high similarity are detected with the programme LFASTA which seeks the best local identities (Pearson and Lipman, PNAS 85: 2444-2448 (1988)). The two clones which were immunoreactive vis-á-vis 2G2G10 made it possible to clearly locate the epitope recognized by 2G2G10 and 8B4H7 in the 199-208 region of HBsAg (FIG. 1). In fact, HWWKHPTRYSLG has (SEQ ID NO: 3) 4 residues identical to and 3 residues similar to the 199-208 sequence whereas HPLKQYWWRPSI (SEQ ID NO: 2) shares 3 identical residues and 1 similar residue with the 201-205 sequence.

Example 8

Detection of the Wild-type HBsAg Antigen and HBsAg Variants Using the 2G2G10 and 8B4H7 Monoclonal Antibodies The format used is a format of sandwich type using the 2G2G10 or 8B4H7 monoclonal antibodies for capture and a goat anti-HBs polyclonal antibody for detection.

Detection of the Wild-type HBsAg Antigen in Patient Serums:

Patient serums supplied by the Société Nationale de Transfusion Sanguine of Lille comprising several sub-types (diluted samples) were tested with the 2G2G10 monoclonal antibodies for capture and a goat anti-HBs polyclonal antibody for detection. The results are presented in Table 2 below. The samples tested are identified according to their sub-type and their origin. The results are expressed as a signal detected with respect to a threshold value. The threshold value corresponds to five times the signal of the negative sample. The values the signal/threshold value of which is greater than 1 are positive.

TABLE 2

| Identification of the sample/sub-types | Signal/Threshold value |
| --- | --- |
| 41 - adw2 - (US + Asia) | 2.91 |
| 42 - adw4 - (Europe + South America) | 3.04 |
| 43 - adr - (Asia) | 2.94 |
| 44 - ayw1 | 3.00 |
| 45 - ayw2 - (Southern Europe) | 3.94 |
| 46 - ayw3 - (Europe-Asia) | 3.42 |
| 47 - ayw3 | 3.07 |
| 48 - ayw4 - (Africa) | 4.02 |
| 49 - ayr - (Japan) | 4.00 |
| 50 - Negative/Diluent of the samples | 0.2 |

Detection of the Wild-type HBsAg Antigen in Plasmas:

Plasmas from the bioMerieux serotheque were tested under the same conditions as above using both the 2G2G10 monoclonal antibodies and the 8B4H7 monoclonal antibodies for capture. The results are presented in Table 3 below. They are expressed as a signal/threshold value. The threshold value corresponds to five times the signal of the negative sample. The values of which the signal/threshold value is greater than 1 are positive.

TABLE 3

| Sample | 2G2G10 // signal/threshold value | 8B4H7 // signal/threshold value |
| --- | --- | --- |
| MAP 52 1/600 | 25.7 | 29.4 |
| MAP 97 1/50000 | 24.6 | 36.1 |
| MAP 59 1/3000 | 42.2 | 43.0 |
| MAP 62 1/7000 | 46.0 | 47.6 |
| MAP 64 1/6000 | 54.7 | 70.7 |
| H80 1/7000 | 58.9 | 56.9 |
| I44519 1/6000 | 52.2 | 54.0 |
| I44344 1/16000 | 62.7 | 69.3 |

Detection of the HbsAg Variants:

The 2G2G10 antibody was tested for its capacity to detect HBsAg mutants from culture supernatants of the recombinant HBsAg variants which were obtained from Dr Carman and prepared according to the method described previously by Ireland et al., (Hepatology 31: 1176-1181(2000)).

The assays were carried out using a fluoro-immunoenzymatic qualitative test developed on the Vidas (registered trademark) automatic analyser (Weber et al., Journal of Virological Methods 42: 63-74 (1993); Mikkelsen et al., Gynecologic Obstetric Investigation 41: 35-40 (1996)). This two-stage capture test was carried out as follows:

The 2G2G10 antibody was fixed on the solid phase receptacle (SPR) at the final concentration of 10 µg/ml. The SPR was then incubated simultaneously with the culture supernatants containing the recombinant proteins corresponding to the different variants and the anti-HBsAg biotinylated goat polyclonal antibody. The second stage then used the alkaline streptavidin-phosphatase conjugate for the fluorometric reaction.

As shown by Table 4, in comparison to 6H6B6, another anti-HBsAg antibody, the 2G2G10 antibody is capable of detecting the different variants tested. In fact, the BA3.2 and T5N samples carry respectively the C124R and T23N mutations which affect, as reported by Ireland et al., (Hepatology 31: 1176-1181 (2000)) the secretion of the antigen in the culture supernatants tested. The absence of detection of these two supernatants cannot therefore be taken into account.

TABLE 4

Reactivity of the anti-HBsAg antibodies vis-à-vis HbsAg variants.

| Mutations in the MHR | Sample | 2G2G10 | 6H6B6 |
| --- | --- | --- | --- |
| Standard sequence | Gly D | 3.3 | 3.0 |
| Standard sequence | Gly Y | 4.9 | 4.3 |
| control plasmid[a] | | 0.2 | 0.3 |
| P120T | BA 2.4 | 3.3 | 3.5 |
| C121R | J1[a] | 6.7 | 27.5 |
| T123N | BA 3.4 | 2.2 | 0.3 |
| T123N/C124R | BA 3.2[a] | 0.2 | 0.3 |
| M133T | SA7 | 3.0 | 2.1 |
| F134L | J2 | 2.3 | 3.0 |
| D144A | AP 3.1 | 4.7 | 0.7 |
| G145R | Arg 1.2 | 7.2 | 0.4 |
| Q129R/G130N/A166V | SA6 | 4.6 | 2.6 |
| Q30R/S53L/L98V/Q101R/S210T | HK188 | 27.4 | 24.2 |
| S143L | 1043 Sp | 3.0 | 0.7 |
| P127A/S143L | 1157 Sp | 3.4 | 0.3 |
| P120S/S143L | 1056 Sp | 1.8 | 0.5 |
| Y100S/T118V/R122K/M133I/Y134N/P142S/S143L/G145K | M5 | 2.0 | 0.7 |
| polysubstitution including D144E | PA17 | 2.5 | 2.3 |
| D99N/122NT123/G145R | T5N[a] | 0.2 | 0.3 |

MHR: signifies major hydrophilic region.

The results are expressed by the average duplicate signal/a threshold value. For each antibody, the threshold value was defined by the average duplicate signal obtained with 0.16 ng/ml of purified plasmatic HBsAg of the sub-types, ad/ay.

[a]Non-diluted samples.

The invention claimed is:

1. An isolated monoclonal antibody that binds specifically to a wild-type hepatitis B surface antigen (HBsAg) and to at least one mutant form of HBsAg,
wherein said monoclonal antibody binds specifically to a conformational epitope formed by a peptide sequence of said wild-type HBsAg or at least one mutant form of HBsAg, and said peptide sequence consists of the amino acids of the 199-208 region of the HBsAg, as set forth in SEQ ID NO: 5.

2. The isolated monoclonal antibody of claim 1, wherein said monoclonal antibody binds specifically to said wild-type HBsAg and to at least two mutant forms of HBsAg.

3. The isolated monoclonal antibody of claim 1, wherein said monoclonal antibody binds specifically to said wild-type HBsAg and to more than two mutant forms of HBsAg.

4. The isolated monoclonal antibody of claim 1, wherein said monoclonal antibody binds specifically to at least one mutant form of HBsAg, and said mutant form of HBsAg comprises at least one amino acid substitution in the "a" determinant of the HBsAg antigen.

5. The isolated monoclonal antibody according to claim 4, wherein said monoclonal antibody binds specifically to at least one mutant form of HBsAg, and said mutant form of HBsAg comprises at least one amino acid substitution in the "a" determinant of HBsAg at positions 127, 133, 134, 142, 143, 144 or 145 of the HBsAg, as set forth in SEQ ID NO: 5.

6. The isolated monoclonal antibody according to claim 5, wherein said monoclonal antibody binds specifically to at least one mutant form of HBsAg, and said mutant form of HBsAg comprises at least one amino acid substitution at positions 100, 118, 120, 122 of the HBsAg, as set forth in SEQ ID NO: 5.

7. The isolated monoclonal antibody according to claim 4, wherein said monoclonal antibody binds specifically to at least one mutant form of HBsAg, and said mutant form of HBsAg comprises at least one substitution corresponding to a replacement of a glycine by an arginine at position 145 of the HBsAg, as set forth in SEQ ID NO: 5.

8. The isolated monoclonal antibody according to claim 4, wherein said monoclonal antibody binds specifically to at least one mutant form of HBsAg antigen, and said HBsAg comprises a substitution of a tyrosine by a serine at position 100 of the HBsAg, a substitution of a threonine by a valine at position 118 of the HBsAg, a substitution of an arginine by a lysine at position 122 of the HBsAg, a substitution of a methionine by an isoleucine at position 133 of the HBsAg, a substitution of a tyrosine by an asparagine at position 134 of the HBsAg, a substitution of a proline by a serine at position 142 of the HBsAg, a substitution of a serine by a leucine at position 143 of the HBsAg, or a substitution of a glycine by a lysine at position 145 of the HBsAg, as set forth in SEQ ID NO: 5.

9. An isolated monoclonal antibody that binds specifically to a wild-type hepatitis B surface antigen (HBsAg) and to at least one mutant form of HBsAg carrying an "a" determinant encoded by sequences having point mutations at the level of one or more codons encoding for the amino acids 127, 133, 134, 142, 143, 144 and 145 of the HBsAg antigen, as set forth in SEQ ID NO: 5, wherein said monoclonal antibody binds specifically to a conformational epitope formed by a peptide sequence of said wild-type HBsAg antigen and said at least one mutant form of HBsAg, and said peptide sequence consists of the amino acids of the 199-208 region of the HBsAg, as set forth in SEQ ID NO: 5.

10. The isolated monoclonal antibody according to claim 1, wherein said monoclonal antibody is a G class immunoglobulin.

11. A fragment of the isolated monoclonal antibody according to claim 1, said fragment being selected from the group consisting of:

Fab,
Fab',
F(ab)2 and
sFv.

12. The isolated monoclonal antibody according to claim 1, wherein said antibody is obtained by a process, comprising:

cultivating a hybridoma, wherein said hybridoma produces said isolated monoclonal antibodies according to claim 1 in vitro or in vivo, or is obtained by immunizing a mammalian animal with a wild-type hepatitis B antigen (HBsAg) or a mutant form of HBsAg, optionally in the form of a fragment or of an appropriate antigen, immortalizing the antibody-producing cells in order to form hybridomas, screening the hybridoma cultures against the wild-type HBsAg or at least one mutant form HBsAg, optionally in the form of a fragment or of an appropriate antigen, and selecting the hybridomas which produce antibodies which bind to the wild-type HBsAg and said at least one mutant form of HBsAg;

and recovering the monoclonal antibodies from the in vitro or in vivo culture medium.

13. A composition which comprises at least one isolated monoclonal antibody as defined in claim 1 or a fragment of said antibody thereof, said fragment being selected from the group consisting of:

Fab,
Fab',
F(ab)2 and
sFv.

14. The composition according to claim 11, wherein said composition is a diagnostic composition and further comprises at least one other monoclonal or polyclonal antibody for the detection of the HBsAg.

15. The composition according to claim 13, wherein said composition is an anti-serum.

16. The antiserum according to claim 15, further comprising at least one other monoclonal antibody or polyclonal antibody or a mixture of anti-HBsAg monoclonal and polyclonal antibodies.

* * * * *